United States Patent
Tomita et al.

(10) Patent No.: US 10,456,337 B2
(45) Date of Patent: Oct. 29, 2019

(54) OIL-IN-OIL TYPE COSMETIC COMPOSITION

(71) Applicant: SHISEIDO COMPANY, LTD., Tokyo (JP)

(72) Inventors: Noriko Tomita, Yokohama (JP); Reiji Miyahara, Yokohama (JP); Hiroyuki Kakoki, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/207,069

(22) Filed: Jul. 11, 2016

(65) Prior Publication Data

US 2016/0317402 A1 Nov. 3, 2016

Related U.S. Application Data

(63) Continuation of application No. 12/996,977, filed as application No. PCT/JP2009/002667 on Jun. 12, 2009, now abandoned.

(30) Foreign Application Priority Data

Jun. 12, 2008 (JP) .................................. 2008-153819

(51) Int. Cl.
| | | |
|---|---|---|
| *A61K 8/06* | (2006.01) | |
| *A61K 8/891* | (2006.01) | |
| *A61Q 1/06* | (2006.01) | |
| *A61K 8/36* | (2006.01) | |
| *A61K 8/25* | (2006.01) | |
| *A61K 8/31* | (2006.01) | |
| *A61K 8/73* | (2006.01) | |

(52) U.S. Cl.
CPC ................... *A61K 8/06* (2013.01); *A61K 8/25* (2013.01); *A61K 8/31* (2013.01); *A61K 8/361* (2013.01); *A61K 8/73* (2013.01); *A61K 8/891* (2013.01); *A61Q 1/06* (2013.01); *A61K 2800/20* (2013.01)

(58) Field of Classification Search
CPC ............. A61K 8/06; A61K 8/891; A61Q 1/06
See application file for complete search history.

(56) References Cited

U.S. PATENT DOCUMENTS

| | | | |
|---|---|---|---|
| 4,780,145 A | 10/1988 | Mori et al. | |
| 5,106,625 A | 4/1992 | Yamamoto et al. | |
| 2001/0031269 A1* | 10/2001 | Arnaud | A61K 8/365 424/401 |
| 2003/0199660 A1* | 10/2003 | Sakuta | A61K 8/89 528/25 |
| 2005/0002890 A1 | 1/2005 | Gardel et al. | |
| 2005/0129638 A1* | 6/2005 | Dumousseaux | A61K 8/29 424/63 |

FOREIGN PATENT DOCUMENTS

| | | |
|---|---|---|
| DE | 4025040 | 2/1991 |
| EP | 0 388 582 | 1/1990 |
| EP | 0 736 545 | 4/1996 |
| EP | 1 514 533 | 9/2004 |
| JP | 63-216817 | 9/1988 |
| JP | 8-26936 | 1/1996 |
| JP | WO 96/40044 | 12/1996 |
| JP | 9-48709 | 2/1997 |
| JP | WO 97/16157 | 5/1997 |
| JP | 9-235210 | 9/1997 |
| JP | 11-255616 | 9/1999 |
| JP | 2000-53530 | 2/2000 |
| JP | 2001-199846 | 7/2001 |
| JP | 2003-313724 | 7/2003 |
| JP | 2003212724 | 7/2003 |
| JP | 2005-350439 | 12/2005 |
| JP | 2007-238578 | 9/2007 |
| JP | 2007-277189 | 10/2007 |

OTHER PUBLICATIONS

European Search Report for Appln. Serial No. 09762283.1 dated Jul. 2, 2012, 6 pages—English.
Japanese Office Search Report for PCT/JP2009/002667 dated Sep. 8, 2009, (JP and English 4 pages).

* cited by examiner

*Primary Examiner* — Anna R Falkowitz
(74) *Attorney, Agent, or Firm* — Andrew F. Young, Esq.; Lackenbach Siegel, LLP

(57) ABSTRACT

The present invention provides an oil-in-oil type cosmetic composition that has excellent transfer resistance after application, a luster, favorable spreadability during application, and also excellent stability. The oil-in-oil type cosmetic composition comprises (a) 5 to 80% by mass of non-volatile hydrocarbon oil, (b) 1 to 70% by mass of non-volatile silicone oil, and (c) 0.1 to 10% by mass of dextrin fatty acid ester. Preferably, the non-volatile hydrocarbon oil (a) and the non-volatile silicone oil (b) are formulated at a ratio (mass ratio) of (a)/[(a)+(b)]=0.4 to 0.8.

15 Claims, No Drawings

OIL-IN-OIL TYPE COSMETIC COMPOSITION

CROSS REFERENCE TO RELATED APPLICATIONS

This Application relates to and is a continuation of U.S. Ser. No. 12/996,977 filed Dec. 8, 2010, the entire contents of which are incorporated herein by reference which in turn claims priority from International Ser. No. PCT/JP2009/002667 filed Jun. 12, 2009, the entire contents of which are incorporated herein by reference, and which in turn claims priority from JP Ser. No. 2008-153819 filed Jun. 12, 2008

FIGURE FOR PUBLICATION

None

BACKGROUND OF THE INVENTION

1. Field of the Invention

The present invention relates to an oil-in-oil type cosmetic composition. More specifically, the present invention relates to an oil-in-oil type cosmetic composition that has excellent transfer resistance and favorable stability without losing a moisture or a luster.

2. Description of the Related Art

Conventional lipstick compositions have presented the problem of indirect smearing that causes a lipstick applied on lips to be transferred onto a site such as a cup upon contact with the lips. By contrast, lipstick compositions having so-called indirect smearing-proof effect that causes little indirect smearing have been developed.

For example, Patent Document 1 discloses a transfer-resistant cosmetic composition comprising: a volatile hydrocarbon solvent; a non-volatile silicone compound that can be dissolved or dispersed in the volatile hydrocarbon solvent; and non-volatile hydrocarbon oil that is dissolved in the volatile solvent and is incompatible with the non-volatile silicone compound, wherein the non-volatile hydrocarbon oil has a certain solubility parameter.

However, this transfer-resistant cosmetic composition has room for improvement in stability. Due to its large content of wax, usability in a liquid state cannot be obtained, and also luster is insufficient.

Patent Document 2 discloses a lipstick composition having transfer resistance, comprising perfluoropolyether-type non-volatile oil and volatile oil, which are incompatible with each other. In this Patent Literature 2, oils are separated during application to a support to move onto a first composition.

However, the first composition is in a solid state due to a considerable amount of wax formulated therein. Thus, a sufficient luster or moisture cannot be obtained. Moreover, for this system, the incompatible oil phases are difficult to favorably disperse, resulting in the problem of stability against sweating or the like.

Patent Document 3 discloses a stick cosmetic having transfer resistance, comprising a silicone surfactant formulated in combination with volatile oil, wherein these ingredients are favorably dispersed in a pigment.

However, this stick cosmetic has a large proportion of the volatile oil in the composition and thus has the disadvantage that its matte finish tends to provide a feeling of dryness on lips.

Patent Document 4 discloses a one-phase composition for lipsticks, comprising volatile oil and a silicone resin.

However, this composition for lipsticks tends to increase a feeling of dryness with a lapse of time after evaporation of the volatile oil, although it has improved transfer resistance. Moreover, a film of the resin remains on lips, leaving a filmy feeling or tightness. The composition further has the disadvantage that the obtained smear is matte.

Patent Document 5 discloses an oil-in-oil type emulsified composition comprising: continuous-phase oil comprising a silicone coating agent, volatile silicone oil, non-volatile silicone oil in a liquid state, and an emulsifying agent; and dispersion-phase oil comprising ester oil and a color material, wherein the amounts of the continuous-phase oil and the dispersion-phase oil formulated are at a dispersion-phase oil/(dispersion-phase oil+continuous-phase oil) ratio of 0.05 to 0.5.

However, this oil-in-oil type emulsified composition tends to have unevenness in color due to the presence of the color material in the dispersion phase. Furthermore, for this system, stability may be difficult to maintain over time.

Patent Document 6 discloses the technique of preventing color transfer by applying a lipstick and then further applying thereonto a lip coat comprising particular dimethylpolysiloxane and silicic anhydride.

However, this technique has presented problems in the complicated two-product use of the applied usual lipstick and the further applied additional lip coat and also in poor portability.

PRIOR PUBLICATIONS AND PATENT DOCUMENTS

Patent Document 1: JP-A-2001-199846
Patent Document 2; WO 96/40044
Patent Document 3: WO 97/16157
Patent Document 4: JP-A-Hei 9-48709
Patent Document 5: JP-A-2000-53530
Patent Document 6: JP-A-Hei 8-26936

ASPECTS AND SUMMARY OF THE INVENTION

Problems to be Solved by the Invention

An object of the present invention is to provide an oil-in-oil type cosmetic composition that has transfer resistance and further has an improved luster after application and also excellent stability.

Means for Solving the Problem

The present inventors have conducted diligent studies and consequently found that: a stable oil-in-oil type composition is obtained by allowing non-volatile hydrocarbon oil and non-volatile silicone oil, which are hardly compatible with each other, to be contained therein and further formulating dextrin fatty acid ester; and the obtained oil-in-oil type cosmetic composition has favorable spreadability during application, with its transfer resistance after application maintained.

Specifically, the present invention provides an oil-in-oil type cosmetic composition comprising
 (a) 5 to 80% by mass of non-volatile hydrocarbon oil,
 (b) 1 to 70% by mass of non-volatile silicone oil, and
 (c) 0.1 to 10% by mass of dextrin fatty acid ester.

In the present invention, it is preferred that the non-volatile hydrocarbon oil (a) and the non-volatile silicone oil (b) should be formulated at a ratio (mass ratio) of (a)/{(a)+(b)}=0.4 to 0.8.

In the present invention, it is preferred that the oil-in-oil type cosmetic composition should further comprise 1 to 30% by mass of semi-solid oil.

Effects of the Invention

An oil-in-oil type cosmetic composition of the present invention has excellent transfer resistance after application, a luster, favorable spreadability during application, and also excellent stability.

The above, and other objects, features and advantages of the present invention will become apparent from the following description read in conjunction with the accompanying drawings, in which like reference numerals designate the same elements.

BRIEF DESCRIPTION OF THE DRAWINGS

None

DETAILED DESCRIPTION OF THE PREFERRED EMBODIMENTS

Reference will now be made in detail to several embodiments of the proposed invention that are illustrated in the description below.

In the present invention, a stable oil-in-oil type composition can be obtained by allowing non-volatile hydrocarbon oil and non-volatile silicone oil, which are hardly compatible with each other, to be contained therein and further formulating dextrin fatty acid ester. In the oil-in-oil type cosmetic composition of the present invention, the non-volatile hydrocarbon oil such as polybutene constitutes continuous-phase oil, while the non-volatile silicone oil such as methylphenylpolysiloxane constitutes dispersion-phase oil. A color material is dispersed in the continuous-phase oil in relation to surface wettability. In the oil-in-oil type cosmetic composition of the present invention, the silicone oil and the hydrocarbon oil maintain a stable oil-in-oil state in a container before use, even without being separated from each other. After application, the non-volatile silicone oil comes up to the surface, and this separated non-volatile silicone oil covers an adherent layer of the non-volatile hydrocarbon oil. Therefore, the resulting composition has transfer resistance and offers a favorable luster. This separation of the non-volatile silicone oil is further promoted by means of pressure applied by rubbing lips against each other during application. The further formulation of volatile hydrocarbon such as isododecane, which is compatible with both the ingredients, can improve spreadability during application, with transfer resistance after application and stability maintained.

Moreover, the present invention does not require formulating a silicone resin, a large amount of wax, or volatile oil and can therefore achieve a luster texture and a moisture feel, as with liquid glosses. Particularly, when the composition of the present invention is used as a lipstick, it saves labor such as two-product use of a lipstick and a lip coat and exerts the effects of long staying even in one-product use, offering a luster, and hardly smearing a cup or the like.

(a) Non-Volatile Hydrocarbon Oil

Examples of the non-volatile hydrocarbon oil (a) used in the present invention include hydrogenated polyisobutene, polybutene, polyisobutylene, polyisoprene, liquid paraffin, squalane, hydrogenated polydecene, and Vaseline. Of them, particularly, polybutene is preferable, and polybutene having a molecular weight of 1000 to 2650 is more preferable.

The amount of the non-volatile hydrocarbon oil (a) formulated is 5 to 80% by mass, preferably 10 to 70% by mass, more preferably 20 to 60% by mass. When the amount of the non-volatile hydrocarbon oil formulated is too small, the resulting composition poorly moisturizes. When the amount of the non-volatile hydrocarbon oil formulated is too large, the resulting composition tends to be poorly spreadable, have increased stickiness and poor transfer resistance, and also poorly color.

(b) Non-Volatile Silicone Oil

The non-volatile silicone oil (b) can be any of those hardly compatible with the hydrocarbon oil and is appropriately selected for an oil-in-oil type, depending on the type of the hydrocarbon oil formulated in combination therewith. Examples of such non-volatile silicone oil include methylphenylpolysiloxane, dimethicone, and fluorine-modified alkyl silicone. Of them, particularly, methylphenylpolysiloxane is preferable, and methylphenylpolysiloxane having a viscosity of 300 to 500 cs is more preferable.

The amount of the non-volatile silicone oil (b) formulated is 1 to 70% by mass, preferably 5 to 60% by mass, more preferably 10 to 50% by mass. When the amount of the non-volatile silicone oil formulated is too small, the resulting composition tends to have poor transfer resistance. When the amount of the non-volatile silicone oil formulated is too large, the resulting composition tends to come off over time, albeit with an increased luster.

In the present invention, it is preferred that the non-volatile hydrocarbon oil (a) and the non-volatile silicone oil (b) should be formulated at a ratio (mass ratio) of (a)/{(a)+(b)}=0.4 to 0.8. When the proportion of the ingredient (a) is too large with respect to the {(a)+(b)} moiety, the resulting composition is poorly spreadable, has increased stickiness and poor transfer resistance, and also poorly colors. When the proportion of the ingredient (a) is too small, i.e., the proportion of the ingredient (b) in (a)+(b) is increased, the resulting composition tends to poorly moisturize, albeit with an increased luster.

(c) Dextrin Fatty Acid Ester

The dextrin fatty acid ester (c) is ester of dextrin and higher fatty acid, and this higher fatty acid has the number of carbon atoms selected from C12 to C22. The higher fatty acid may partially contain fatty acid having the number of carbon atoms of C6 to C10, as long as it comprises fatty acid having the number of carbon atoms of C12 to C22. Examples of such dextrin fatty acid ester include palmitic acid dextrin, myristic acid dextrin, and (palmitic acid/ethylhexanoic acid)dextrin. Commercially available products such as trade names Rheopearl KL, Rheopearl KL2, Rheopearl TT, Rheopearl TT2, and Rheopearl MKL2 (all manufactured by Chiba Flour Milling Co., Ltd.) can be used.

The amount of the dextrin fatty acid ester (c) formulated is 0.1 to 10% by mass, preferably 0.5 to 8% by mass, more preferably 1 to 5% by mass. When the amount of the dextrin fatty acid ester formulated is too small, the resulting composition is poorly stable. When the amount of the dextrin fatty acid ester formulated is too large the resulting composition is sticky.

In the present invention, the further formulation of volatile hydrocarbon (d) enhances spreadability during application.

The volatile hydrocarbon (d) is preferably any of those soluble in both the non-volatile hydrocarbon oil (a) and the non-volatile silicone oil (b). Examples thereof can include volatile oils having 8 to 16 carbon atoms and mixtures thereof. Particularly, these volatile hydrocarbons are selected from branched C8-C16 alkanes, branched C8-C16 esters, and mixtures thereof. Preferable examples of such volatile hydrocarbon include C8-C16 isoparaffin obtained particularly from petroleum. Commercially available products such as "Isopar" (isoparaffin solvent, manufactured by Exxon Mobil Corp.), and "Permethyl 99A and Permethyl 101A" (manufactured by EC Eldorchemie, sold by NIHON KOKEN KOGYO CO., LTD.) may be used. Particularly, isododecane or isohexadecane, isohexyl neopentanoate, and mixtures thereof are preferable, and isododecane is more preferable.

The formulation of the volatile hydrocarbon (d) enhances spreadability during application. The preferable amount of the volatile hydrocarbon (d), when formulated, is 0.1 to 50% by mass, preferably 1 to 30% by mass.

In the present invention, the further formulation of silicic anhydride (e) improves a luster during application.

The silicic anhydride (e) is preferably an ultra-fine particle of silicic anhydride having an average primary particle size of 1 to 50 nm. Examples thereof include Aerosil 200, Aerosil 300, Aerosil R972, Aerosil R974, and Aerosil RY200 (manufactured by Nippon Aerosil Co., Ltd.). The silicic anhydride used in the present invention may be hydrophilic or may be hydrophobized by silylation or the like.

The preferable amount of the silicic anhydride (e), when formulated, is 10% by mass or smaller, preferably 0.1 to 5% by mass.

In the present invention, a color material is formulated in addition to the essential ingredients described above. The color material can be any of color materials usually used in lipsticks and may be in a powdery or lake (state kneaded with oil) form. A pigment, which may be an inorganic pigment, an organic pigment, or a pearlizing agent, is more wettable in the hydrocarbon oil than in the silicone oil and eventually moves spontaneously to the hydrocarbon oil as a continuous phase. The amount of the color material formulated is 0.01 to 30% by mass, preferably 0.1 to 20% by mass.

In the present invention, it is preferred that the composition should further comprise semi-solid oil (f) or microcrystalline wax. The formulation of the semi-solid oil or the microcrystalline wax reduces stickiness after application of the lipstick and also enhances duration.

The semi-solid oil (f) specifically refers to oil in a semi-solid state having a solidity of 0.1 to 10 N at 25° C. In the measurement of this solidity, a value measured using a rheometer (manufactured by Rheotech Co., Ltd.) with a pressure-sensitive axis of 5 $\phi$ at a penetration rate of 2 cm/min and a penetration depth of 3 mm was used. Thus, the semi-solid oil does not include highly viscous liquid oil such as polybutene, or oil agents such as hydrogenated castor oil and hard lanolin, which are hard at room temperature.

The semi-solid oil has a melting point of preferably 30 to 52° C. The measurement method of the melting point follows Article 3 of The Japanese Standards of Cosmetic Ingredients. Specifically, first, a sample is melted by gradual heating to 90 to 92° C. with well stirring. After the termination of heating, the sample is allowed to cool to a temperature 8 to 10° C. higher than the melting point. Subsequently, a thermometer (thermometer for petrolatum melting point specified by B7410 of Japanese Industrial Standards) is cooled to 5° C., and its moisture is then wiped off with filter paper. The thermometer is inserted into the sample up to half the mercury bulb thereof, immediately taken out, and allowed to cool in an upright position. When the sample attached thereto has become turbid, the thermometer is dipped for 5 minutes in water with a temperature of 16° C. or lower. Next, the thermometer is inserted into a test tube (25×100 mm) and secured using a cork such that a gap of 15 mm is formed between the lower end of the thermometer and the inside bottom of the test tube. This test tube is placed in a 500-mL beaker containing water of approximately 16° C. and secured such that a gap of 15 mm is formed between the bottom of the test tube and the inside bottom of the beaker. The beaker is heated to at a rate of 2° C./minute until the temperature of the bath reaches 30° C. Subsequently, heating is continued at a rate of 1° C./minute, and the temperature is measured at which a droplet of the sample is removed from the thermometer. This test is conducted three times, and the average of the measurement values is used when they differ by less than 1° C. If the difference is 1° C. or more, the average from 5 measurements is used. The obtained value is defined as a melting point.

Examples of the semi-solid oil include Vaseline, lanolin, plant fats (e.g., shea butter and partially hydrogenated coconut oil), partially hydrogenated jojoba oil, and dimer dilinoleate usually used in cosmetics and specifically include dimer dilinoleate/phytosterol/higher alcohol ester whose alcohol residue contains a phytosteryl group and a linear higher alcohol residue having 16 to 22 carbon atoms. Examples of the dimer dilinoleate include (phytosteryl/behenyl) dimer dilinoleate (trade name: Plandool-PB), (phytosteryl/behenyl/stearyl/cetyl/isostearyl) dimer dilinoleate (trade name: Plandool-H or Plandool-S), and (phytosteryl/behenyl/isostearyl) dimer dilinoleyl dimer dilinoleate (trade name: Plandool-G). Moreover, pentaerythritol tetra(behenate/benzoate/ethylhexanoate), dipentaerythritol hexahydroxystearate, macadamia seed oil polyglyceryl-6 esters behenate, or the like can also be used. Furthermore, the following commercially available products may be used: "COSMOL 168EV, COSMOL 168M, and COSMOL 168AR" (all manufactured by The Nisshin Oillio Group, Ltd.), "YOFCO-MAS", "SOFTISAN 649" (manufactured by Sasol Ltd.), and "Eldew PS-304" (manufactured by Ajinomoto Co., Inc.).

Of them, Vaseline and pentaerythritol tetra(behenate/benzoate/ethylhexanoate) are particularly preferable in terms of the absence of stickiness and long duration. The amount of the semi-solid oil formulated is preferably 3 to 30% by mass, more preferably 6 to 20% by mass.

The amount of the microcrystalline wax formulated is preferably 0.5 to 6% by mass, more preferably 1 to 4% by mass.

The oil-in-oil type cosmetic composition of the present invention can be formulated appropriately with an oil agent, a wax, a powder, a pigment, a dye, a polymer compound, a moisturizer, a perfume, a surfactant, an antioxidant, an antiseptic, and a beauty component, etc., used in usual oil-based cosmetic compositions, in addition to the essential ingredients described above, without impairing the effect of the present invention. Examples of the moisturizer include polyhydric alcoholic moisturizers such as glycerin, propylene glycol, and 1,3-butylene glycol.

Although the wax can be formulated therein, its formulation in a large amount impairs a luster. Thus, the amount of the wax, even if formulated, is preferably 5% by mass or smaller.

Moreover, the formulation of a coating agent in a large amount causes stiffness. Thus, the coating agent is not formulated, or the amount of the coating agent, even if formulated, is preferably 5% by mass or smaller.

The oil-in-oil type cosmetic composition of the present invention can be applied to lipsticks, lip glosses, lip bases, overcoats for lipsticks, lip creams, etc. Particularly, when the oil-in-oil type cosmetic composition of the present invention is used as a color material-formulated lipstick, the oil-in-oil type cosmetic composition is preferable because the resultant lipstick has a combination of coloration effect, transfer resistance, and a luster as with lip glosses.

EXAMPLES

Hereinafter, the present invention will be described more specifically with reference to Examples. However, the present invention is not limited to them by any means. In Examples below, amounts formulated mean % by mass, unless otherwise specified.

In prior to the description of Examples, effect test methods used in the present invention will be described.

(1) Evaluation Test on Usability

Actual usability test was conducted by ten expert panelists. Evaluation items on usability were spreadability during application, a luster, a moisture feel, the absence of stiffness, and transfer resistance and were sensorily evaluated (scored) on 5 scales according to scoring criteria shown below. Based on the average of the scores, samples were assessed on according to evaluation criteria shown below. Moreover, in Examples 9 to 20, the absence of stickiness and duration were evaluated after 2 hours from application.

Evaluation on spreadability during application, a luster, a moisture feel, the absence of stiffness, and transfer resistance was conducted during application or immediately after application, whereas the absence of stickiness and duration were evaluated by evaluating stickiness and the lasting of cosmetic effect after 2 hours from application.

The application method was performed by a method involving: applying a cosmetic composition of the present invention onto lips; and then applying pressure only for 5 seconds by rubbing the upper and lower lips against each other. In the evaluation of transfer resistance, the absence of transfer to a cup was evaluated. In the evaluation of duration, whether the applied state of a lipstick was maintained after 2 hours was assessed by visual observation based on a luster, coloration, a beautiful finish, etc.

(Score)
5: very excellent
4: excellent
3: ordinary
2: poor
1: very poor (Evaluation Criteria)
A: score (average) between 4.0 and 5.0 inclusive
B: score (average) of 3.0 or higher and lower than 4.0
C: score (average) of 2.0 or higher and lower than 3.0
D: score (average) of 1.0 or higher and lower than 2.0

(2) Evaluation Test on Stability Against Separation

Stability against separation in a container in use was evaluated by the following method:

(Evaluation Method)

Formulas described in tables were prepared by a standard method and placed in bottle containers equipped with an applicator. Each composition was used twice a day for 1 week and then evaluated, (Evaluation Criteria)
A: uniform without being separated
B: partially separated but at a level of no importance in use
C: separated with unevenness in color
D: completely separated Examples 1 to 8 and Comparative Examples 1 to 10

Each gloss lipstick was prepared according to formulas shown in Tables 1 to 3 below and evaluated for its usability (spreadability during application, luster, moisture feel, absence of stiffness, and transfer resistance) and stability against separation according to the criteria described above. The results are also shown in Tables 1 to 3.

TABLE 1

| | | Example 1 | Example 2 | Example 3 | Comparative Example 1 | Comparative Example 2 |
|---|---|---|---|---|---|---|
| <Phase A> | Non-volatile hydrocarbon oil | | | | | |
| | Hydrogenated polyisobutene (average molecular weight: 1000) | 35 | 40 | 35 | — | 15 |
| | Hydrogenated polyisobutene (average molecular weight: 2650) | 10 | 10 | 10 | — | — |
| | Color material | | | | | |
| | Red No. 202 | 1 | 1 | 1 | 1 | 1 |
| | Iron oxide | 2 | 2 | 2 | 2 | 2 |
| | Pearlizing agent | | | | | |
| | Mica titanium | 2 | 2 | 2 | 2 | 2 |
| | Extender pigment | | | | | |
| | Mica | — | — | — | — | 8 |
| | Ester oil | | | | | |
| | Octanoin | — | — | — | 10 | — |
| | Glycerin triisostearate | — | — | — | — | 10 |
| <Phase B> | Thickener | | | | | |
| | Palmitic acid dextrin | 3 | 3 | 3 | — | 1 |
| | Silicic anhydride | — | — | 1 | — | — |
| | Wax | | | | | |
| | Ceresin | — | — | — | 5 | — |
| | Microcrystalline wax | — | — | — | 3 | 7 |
| <Phase C> | Volatile hydrocarbon oil | | | | | |
| | Isododecane | 7 | — | 7 | — | — |
| <Phase D> | Non-volatile silicone oil | | | | | |
| | Methylphenylpolysiloxane (500cs) *3 | 40 | 42 | 39 | — | — |
| | Dimethylpolysiloxane (6cs) | — | — | — | 10 | 10 |
| | Silicone coating agent | | | | | |
| | Trimethylsiloxysilicate *1 | — | — | — | 25 | 15 |

TABLE 1-continued

|  | Example 1 | Example 2 | Example 3 | Comparative Example 1 | Comparative Example 2 |
|---|---|---|---|---|---|
| Volatile silicone oil |  |  |  |  |  |
| Cyclomethicone *2 | — | — | — | 42 | 29 |
| Total (% by mass) | 100 | 100 | 100 | 100 | 100 |
| Spreadability | A | B | A | C | C |
| Luster | A | A | A | D | D |
| Moisture feel | A | A | A | D | D |
| Absence of stiffness | A | A | A | D | D |
| Transfer resistance | A | A | A | A | C |
| Stability against separation in container in use | B | B | A | B | B |
| Non-volatile hydrocarbon oil/(non-volatile hydrocarbon oil + non-volatile silicone oil) | 0.53 | 0.54 | 0.54 | 0 | 0.6 |
| Formula system | Oil-in-oil type | Oil-in-oil type | Oil-in-oil type | One-phase type | One-phase type |

TABLE 2

|  |  | Comparative Example 3 | Comparative Example 4 | Comparative Example 5 | Comparative Example 6 | Comparative Example 7 | Comparative Example 8 | Comparative Example 9 | Comparative Example 10 |
|---|---|---|---|---|---|---|---|---|---|
| <Phase A> | Non-volatile hydrocarbon oil |  |  |  |  |  |  |  |  |
|  | Hydrogenated polyisobutene (average molecular weight: 1000) | 35 | 35 | 35 | 35 | 35 | 35 | 35 | 35 |
|  | Hydrogenated polyisobutene (average molecular weight: 2650) | 10 | 10 | 10 | 10 | 10 | 10 | 10 | 10 |
|  | Vaseline | 3 | — | — | — | — | — | — | — |
|  | Color material |  |  |  |  |  |  |  |  |
|  | Red No. 202 | 1 | 1 | 1 | 1 | 1 | 1 | 1 | 1 |
|  | Iron oxide | 2 | 2 | 2 | 2 | 2 | 2 | 2 | 2 |
|  | Pearlizing agent |  |  |  |  |  |  |  |  |
|  | Mica titanium | 2 | 2 | 2 | 2 | 2 | 2 | 2 | 2 |
| <Phase B> | Wax |  |  |  |  |  |  |  |  |
|  | Carnauba wax | — | 3 | — | — | — | — | — | — |
|  | Microcrystalline wax | — | — | 3 | — | — | — | — | — |
|  | Alkyl-modified silicone wax | — | — | — | 3 | — | — | — | — |
|  | Silicone surfactant |  |  |  |  |  |  |  |  |
|  | Polyoxyalkylene-modified organopolysiloxane *4 | — | — | — | — | 3 | — | — | — |
|  | Hydrocarbon surfactant |  |  |  |  |  |  |  |  |
|  | Diglyceryl diisostearate | — | — | — | — | — | 3 | — | — |
|  | diglyceryl triisostearate | — | — | — | — | — | — | 3 | — |
|  | Gelling agent |  |  |  |  |  |  |  |  |
|  | 12-hydroxystearic acid | — | — | — | — | — | — | — | 3 |
|  | Thickener |  |  |  |  |  |  |  |  |
|  | Palmitic acid dextrin | — | — | — | — | — | — | — | — |
|  | Silicic anhydride | 1 | 1 | 1 | 1 | 1 | 1 | 1 | 1 |
| <Phase C> | Volatile hydrocarbon oil |  |  |  |  |  |  |  |  |
|  | Isododecane | 7 | 7 | 7 | 7 | 7 | 7 | 7 | 7 |
| <Phase D> | Non-volatile silicone oil |  |  |  |  |  |  |  |  |
|  | Methylphenylpolysiloxane (500cs) *3 | 39 | 39 | 39 | 39 | 39 | 39 | 39 | 39 |
|  | Total (% by mass) | 100 | 100 | 100 | 100 | 100 | 100 | 100 | 100 |
|  | Spreadability | B | B | B | B | B | B | B | B |
|  | Luster | A | B | B | B | A | A | A | B |
|  | Moisture feel | A | B | B | B | A | A | A | B |
|  | Absence of stiffness | B | B | B | B | B | B | B | B |
|  | Transfer resistance | B | B | B | B | B | B | B | B |
|  | Stability against separation in container in use | D | D | D | D | D | D | D | D |
|  | Non-volatile hydrocarbon oil/(non-volatile hydrocarbon oil + non-volatile silicone oil) | 0.55 | 0.54 | 0.54 | 0.54 | 0.54 | 0.54 | 0.54 | 0.54 |
|  | Formula system | Oil-in-oil type | Oil-in-oil type | Oil-in-oil type | Oil-in-oil type | Oil-in-oil type | Oil-in-oil type | Oil-in-oil type | Oil-in-oil type |

TABLE 3

|  |  | Example 4 | Example 5 | Example 6 | Example 7 | Example 8 |
|---|---|---|---|---|---|---|
| <Phase A> | Non-volatile hydrocarbon oil |  |  |  |  |  |
|  | Hydrogenated polyisobutene (average molecular weight: 1000) | 35 | 35 | 35 | 35 | 35 |
|  | Hydrogenated polyisobutene (average molecular weight: 2650) | 10 | 10 | 10 | 10 | 10 |
|  | Vaseline | 3 | — | — | — | — |
|  | Color material |  |  |  |  |  |
|  | Red No. 202 | 1 | 1 | 1 | 1 | 1 |
|  | Iron oxide | 2 | 2 | 2 | 2 | 2 |
|  | Pearlizing agent |  |  |  |  |  |
|  | Mica titanium | 2 | 2 | 2 | 2 | 2 |
| <Phase B> | Ester oil |  |  |  |  |  |
|  | Glyceryl triisostearate | — | 2 | — | — | — |
|  | Wax |  |  |  |  |  |
|  | Carnauba wax | — | — | 3 | — | — |
|  | Microcrystalline wax | — | — | — | 3 | 7 |
|  | Thickener |  |  |  |  |  |
|  | Palmitic acid dextrin | 3 | 3 | 2 | 2 | 3 |
|  | Silicic anhydride | 1 | 1 | 1 | 1 | 1 |
| <Phase C> | Volatile hydrocarbon oil |  |  |  |  |  |
|  | Isododecane | 7 | 7 | 7 | 7 | 7 |
| <Phase D> | Non-volatile silicone oil |  |  |  |  |  |
|  | Methylphenylpolysiloxane (500cs) *3 | 36 | 37 | 37 | 37 | 32 |
|  | Total (% by mass) | 100 | 100 | 100 | 100 | 100 |
|  | Spreadability | A | A | B | B | C |
|  | Luster | A | A | B | B | C |
|  | Moisture feel | A | A | A | A | C |
|  | Absence of stiffness | A | A | A | A | C |
|  | Transfer resistance | A | A | A | A | B |
|  | Stability against separation in container in use | A | A | B | A | C |
|  | Non-volatile hydrocarbon oil/(non-volatile hydrocarbon oil + non-volatile silicone oil) | 0.57 | 0.55 | 0.55 | 0.55 | 0.58 |
|  | Formula system | Oil-in-oil type | Oil-in-oil type | Oil-in-oil type | Oil-in-oil type | Oil-in-oil type |

The compositions of Examples 1 to 3 had spreadability, a luster, and a moisture feel and were free from stiffness and excellent in transfer resistance and stability against separation. On the other hand, the cosmetic compositions of Comparative Examples 1 and 2, which were formulated with a conventional coating agent, were poorly usable, due to a loss of luster and stiffness.

The compositions of Comparative Examples 3 to 10, which contained no dextrin fatty acid ester, had poor stability against separation, although various waxes or silicone surfactants were combined. On the other hand, the compositions of Examples 4 to 8 could maintain stability owing to dextrin fatty acid ester formulated therein, even when formulated with ester oil and wax.

Examples 9 to 20

Each gloss lipstick was prepared according to formulas shown in Table 4 below and evaluated for its stickiness and duration after 2 hours from application according to the criteria described above. The results are also shown in Tables 4 and 5.

TABLE 4

|  | Example 9 | Example 10 | Example 11 | Example 12 | Example 13 | Example 14 |
|---|---|---|---|---|---|---|
| Hydrogenated polyisobutene (average molecular weight: 1000) | 38 | 35 | 35 | 35 | 35 | 35 |
| Hydrogenated polyisobutene (average molecular weight: 2650) | 10 | 10 | 10 | 10 | 10 | 10 |
| Vaseline | — | 3 | — | — | — | — |
| (Phytosteryl/behenyl) dimer dilinoleate | — | — | 3 | — | — | — |
| Microcrystalline wax | — | — | — | 3 | — | — |
| Pentaerythritol tetra(behenate/benzoate/ethylhexanoate) | — | — | — | — | 3 | — |
| Dipentaerythritol hexahydroxystearate | — | — | — | — | — | 3 |
| Macadamia seed oil polyglyceryl-6 esters behenate | — | — | — | — | — | — |
| Color material | 5 | 5 | 5 | 5 | 5 | 5 |
| Palmitic acid dextrin | 3 | 3 | 3 | 3 | 3 | 3 |
| Silicic anhydride | 1 | 1 | 1 | 1 | 1 | 1 |
| Isododecane | 7 | 7 | 7 | 7 | 7 | 7 |
| Methylphenylpolysiloxane *3 | 36 | 36 | 36 | 36 | 36 | 36 |
| Total (% by mass) | 100 | 100 | 100 | 100 | 100 | 100 |

TABLE 4-continued

|  | Example 9 | Example 10 | Example 11 | Example 12 | Example 13 | Example 14 |
|---|---|---|---|---|---|---|
| Absence of stickiness | B | A | B | B | A | B |
| Duration | B | B | A | A | B | A |

TABLE 5

|  | Example 15 | Example 16 | Example 17 | Example 18 | Example 19 | Example 20 |
|---|---|---|---|---|---|---|
| Hydrogenated polyisobutene (average molecular weight: 1000) | 35 | 32 | 32 | 28 | 18 | 8 |
| Hydrogenated polyisobutene (average molecular weight: 2650) | 10 | 10 | 10 | 10 | 10 | 10 |
| Vaseline | — | — | 6 | 10 | 20 | 30 |
| (Phytosteryl/behenyl) dimer dilinoleate | — | — | — | — | — | — |
| Microcrystalline wax | — | — | — | — | — | — |
| Pentaerythritol tetra(behenate/benzoate/ethylhexanoate) | — | 6 | — | — | — | — |
| Dipentaerythritol hexahydroxystearate | — | — | — | — | — | — |
| Macadamia seed oil polyglyceryl-6 esters behenate | 3 | — | — | — | — | — |
| Color material | 5 | 5 | 5 | 5 | 5 | 5 |
| Palmitic acid dextrin | 3 | 3 | 3 | 3 | 3 | 3 |
| Silicic anhydride | 1 | 1 | 1 | 1 | 1 | 1 |
| Isododecane | 7 | 7 | 7 | 7 | 7 | 7 |
| Methylphenylpolysiloxane *3 | 36 | 36 | 36 | 36 | 36 | 36 |
| Total (% by mass) | 100 | 100 | 100 | 100 | 100 | 100 |
| Absence of stickiness | B | A | A | A | A | A |
| Duration | A | A | A | A | A | B |

As seen from the results of Tables 4 and 5, the formulation of semi-solid oil or microcrystalline wax further enhanced the absence of stickiness and duration. Moreover, among them, Vaseline and pentaerythritol tetra(behenate/benzoate/ethylhexanoate) exerted particularly high effect. Moreover, the semi-solid oil exhibited excellent effect particularly when formulated in an amount of 6 to 20% by mass.

Hereinafter, formulation examples of the oil-in-oil type cosmetic composition of the present invention will be taken. However, the present invention is not limited to these formulation examples by any means and, needless to say, is specified by claims.

Examples 21: Gloss Lipstick in Bottle Container Equipped with Applicator

| Formulated ingredient | % by mass |
|---|---|
| <Phase A> | |
| Hydrogenated polyisobutene | 40 |
| Squalane | 20 |
| Vaseline | 10 |
| Red iron oxide | 1 |
| Red No. 202 | 1 |
| Mica titanium | 1 |
| Diglyceryl diisostearate | 3 |
| Silylated silica | 1 |
| <Phase B> | |
| Palmitic acid dextrin | 3 |
| <Phase C> | |
| Methylphenylpolysiloxane | 20 |

Production Method:

The phase B is dispersed in the phase A by stirring and then dissolved by heating. The phase C is further added thereto and dispersed by stirring to prepare a gloss lipstick.

Examples 22: Gloss Lipstick in Twist- or Push-Type Container

| Formulated ingredient | % by mass |
|---|---|
| <Phase A> | |
| Hydrogenated polyisobutene | 33.9 |
| Red iron oxide | 1 |
| Red No. 202 | 1 |
| Mica titanium | 1 |
| Diglyceryl triisostearate | 3 |
| <Phase B> | |
| Palmitic acid dextrin | 0.1 |
| <Phase C> | |
| Isododecane | 10 |
| <Phase D> | |
| Methylphenylpolysiloxane | 45 |
| Silica 5 | |

Production Method:

The phases A to C were dispersed by stirring and then dissolved by heating. The phase D dispersed by stirring in advance was added thereto and dispersed by stirring to prepare a gloss lipstick.

Examples 23: Gloss Lipstick in Bottle Container Equipped with Applicator

| Formulated ingredient | % by mass |
|---|---|
| <Phase A> | |
| Hydrogenated polyisobutene | 20 |
| Red iron oxide | 1 |
| Mica titanium | 1 |
| 12-hydroxystearic acid | 3 |
| Silica | 5 |
| Alkyl-modified silicone-treated mica | 10 |
| <Phase B> | |
| Palmitic acid dextrin | 10 |
| <Phase C> | |
| Isododecane | 20 |
| <Phase D> | |
| Methylphenylpolysiloxane | 30 |

Production Method:

The phases A to C were dispersed by stirring and then dissolved by heating. The phase D was further added thereto and dispersed by stirring to prepare a gloss lipstick.

Examples 24: Gloss Lipstick in Bottle Container Equipped with Applicator

| Formulated ingredient | % by mass |
|---|---|
| <Phase A> | |
| Hydrogenated polyisobutene | 30 |
| Vaseline | 1 |
| Squalane | 19 |
| Red iron oxide | 1 |
| Mica titanium | 5 |
| Silicic anhydride | 2 |
| <Phase B> | |
| (palmitic acid/2-ethylhexanoic acid)dextrin (trade name: Rheopearl TT, manufactured by Chiba Flour Milling Co., Ltd.) | 10 |
| <Phase C> | |
| Methylphenylpolysiloxane | 30 |
| Silylated silica | 2 |

Production Method:

The phases A to C were dispersed by stirring and then dissolved by heating. The phase D was further added thereto and dispersed by stirring to prepare a gloss lipstick.

Examples 25: Lipstick Charged in Middle Plate

| Formulated ingredient | % by mass |
|---|---|
| <Phase A> | |
| Hydrogenated polyisobutene | 30 |
| Red iron oxide | 1 |

| Formulated ingredient | % by mass |
|---|---|
| Mica titanium | 4 |
| Silylated silica | 3 |
| Alkyl-modified silicone-treated mica | 10 |
| <Phase B> | |
| Myristic acid dextrin (trade name: Rheopearl MKL2) | 5 |
| Palmitic acid dextrin | 5 |
| <Phase C> | |
| Isododecane | 10 |
| <Phase D> | |
| Methylphenylpolysiloxane | 30 |
| Silica | 2 |

Production Method:

The phases A to C were dispersed by stirring and then dissolved by heating. The phase D was further added thereto and dispersed by stirring to prepare a lipstick.

Examples 26: Gloss Lipstick in Bottle Container Equipped with Applicator

| Formulated ingredient | % by mass |
|---|---|
| <Phase A> | |
| Hydrogenated polyisobutene | 30 |
| Squalane | 10 |
| Red iron oxide | 2 |
| Mica titanium | 3 |
| Silylated silica | 3 |
| Alkyl-modified silicone-treated mica | 5 |
| <Phase B> | |
| Palmitic acid dextrin | 5 |
| <Phase C> | |
| Isododecane | 10 |
| <Phase D> | |
| Fluorine-modified methylphenylpolysiloxane (INCI Name: fluoroalkyl diphenyl dimethicone) | 30 |
| Silica | 2 |

Production Method:

The phases A to C were dispersed by stirring and then dissolved by heating. The phase D was further added thereto and dispersed by stirring to prepare a gloss lipstick.

Examples 27: Gloss Lipstick in Bottle Container Equipped with Applicator

| Formulated ingredient | % by mass |
|---|---|
| <Phase A> | |
| Hydrogenated polyisobutene | 35 |
| squalane | 10 |
| Red iron oxide | 2 |
| Mica titanium | 3 |
| Silylated silica | 3 |
| Alkyl-modified silicone-treated mica | 5 |

| Formulated ingredient | % by mass |
|---|---|
| <Phase B> | |
| Palmitic acid dextrin | 5 |
| <Phase C> | |
| Dimethylpolysiloxane (trade name: Silicone KF-96A-300, manufactured by Shin-Etsu Chemical Co., Ltd.) | 35 |
| Silica | 2 |

Production Method:

The phases A to B were dispersed by stirring and then dissolved by heating. The phase C was further added thereto and dispersed by stirring to prepare a gloss lipstick.

The cosmetic compositions of Examples 21 to 27 were excellent in all of spreadability, a luster, a moisture feel, and transfer resistance.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

The invention claimed is:

1. A cosmetic composition comprising:
   (a) 10 to 70% by mass of non-volatile hydrocarbon oil,
   (b) 5 to 60% by mass of methylphenylpolysiloxane, and
   (c) 0.5 to 8% by mass of an ester of dextrin and fatty acid having 12-22 carbon atoms,
   wherein the ester of dextrin stabilizes an oil-in-oil emulsion of the non-volatile hydrocarbon and the methylphenylpolysiloxane, wherein the cosmetic composition does not comprise a volatile hydrocarbon oil, wherein the non-volatile hydrocarbon oil comprises a hydrogenated polyisobutene having a molecular weight of 1,000 to 2,650, and
   wherein the non-volatile hydrocarbon oil (a) and methylphenylpolysiloxane (b) are formulated at a ratio (mass ratio) of (a)/[(a)+(b)]=0.5 to 0.8.

2. The cosmetic composition according to claim 1, wherein the methylphenylpolysiloxane has a viscosity of 300 to 500 cs.

3. The cosmetic composition according to claim 1, further comprising 0.1 to 5% by mass of silicic anhydride.

4. The cosmetic composition according to claim 1, further comprising 1 to 30% by mass of semi-solid oil.

5. An A cosmetic composition comprising:
   (a) 10 to 70% by mass of non-volatile hydrocarbon oil including a hydrogenated polyisobutene having a molecular weight of 1,000 or to 2,650,
   (b) 5 to 60% by mass of methylphenylpolysiloxane,
   (c) 0.5 to 8% by mass of an ester of dextrin and fatty acid having 12-22 carbon atoms,
   (d) 0.1 to 5% by mass of silicic anhydride, and
   (e) 1 to 30% by mass of semi-solid oil,
   wherein the cosmetic composition does not comprise a volatile hydrocarbon oil, and
   wherein the non-volatile hydrocarbon oil (a) and methylphenylpolysiloxane (b) are formulated in an oil-in-oil emulsion at a ratio (mass ratio) of (a)/[(a)+(b)]=0.5 to 0.8.

6. A lip cosmetic comprising:
   (a) 10 to 70% by mass of non-volatile hydrocarbon oil including a hydrogenated polyisobutene having a molecular weight of 1,000 to 2,650,
   (b) 5 to 60% by mass of methylphenylpolysiloxane,
   (c) 0.5 to 8% by mass of an ester of dextrin and fatty acid having 12-22 carbon atoms,
   (d) 0.1 to 5% by mass of silicic anhydride, and
   (e) 1 to 30% by mass of semi-solid oil,
   wherein the lip cosmetic does not comprise a volatile hydrocarbon oil, and wherein the non-volatile hydrocarbon oil (a) and methylphenylpolysiloxane (b) are formulated in an oil-in-oil emulsion at a ratio (mass ratio) of (a)/[(a)+(b)]=0.5 to 0.8.

7. The cosmetic composition according to claim 1, wherein the ester of dextrin and fatty acid includes at least one selected from the group consisting of palmitic acid dextrin, myristic acid dextrin, and (palmitic acid/ethylhexanoic acid) dextrin.

8. The cosmetic composition according to claim 5, wherein the ester of dextrin and fatty acid includes at least one selected from the group consisting of palmitic acid dextrin, myristic acid dextrin, and (palmitic acid/ethylhexanoic acid) dextrin.

9. The lip cosmetic according to claim 6, wherein the ester of dextrin and fatty acid includes at least one selected from the group consisting of palmitic acid dextrin, myristic acid dextrin, and (palmitic acid/ethylhexanoic acid) dextrin.

10. The cosmetic composition according to claim 4, wherein the semisolid oil is at least one selected from the group consisting of Vaseline, (phytosteryl/behenyl) dimer dilinoleate, pentaerythritol tetra(behenate/benzoate/ethylhexanoate), dipentaerythritol hexahydroxystearate, and macadamia seed oil polyglyceryl-6 esters behenate.

11. The oil in oil cosmetic composition according to claim 5, wherein the semisolid oil is at least one selected from the group consisting of Vaseline, (phytosteryl/behenyl) dimer dilinoleate, pentaerythritol tetra(behenate/benzoate/ethylhexanoate), dipentaerythritol hexahydroxystearate, and macadamia seed oil polyglyceryl-6 esters behenate.

12. The lip cosmetic according to claim 6, wherein the semisolid oil is at least one selected from the group consisting of Vaseline, (phytosteryl/behenyl) dimer dilinoleate, pentaerythritol tetra(behenate/benzoate/ethylhexanoate), dipentaerythritol hexahydroxystearate, and macadamia seed oil polyglyceryl-6 esters behenate.

13. The cosmetic composition according to claim 1, further comprising 0.5 to 6% by mass of microcrystalline wax.

14. The cosmetic composition according to claim 5, further comprising 0.5 to 6% by mass of microcrystalline wax.

15. The lip cosmetic according to claim 6, further comprising 0.5 to 6% by mass of microcrystalline wax.

* * * * *